(12) United States Patent
Bevis et al.

(10) Patent No.: US 7,355,709 B1
(45) Date of Patent: Apr. 8, 2008

(54) METHODS AND SYSTEMS FOR OPTICAL AND NON-OPTICAL MEASUREMENTS OF A SUBSTRATE

(75) Inventors: Christopher F. Bevis, Los Gatos, CA (US); Gary Dickerson, Cupertino, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 257 days.

(21) Appl. No.: 11/063,228

(22) Filed: Feb. 22, 2005

Related U.S. Application Data

(60) Provisional application No. 60/546,907, filed on Feb. 23, 2004.

(51) Int. Cl.
*G01B 11/00* (2006.01)

(52) U.S. Cl. ..................................................... 356/390

(58) Field of Classification Search ................. 356/72, 356/73, 390, 237.1, 243.4, 247; 250/311; 702/85
See application file for complete search history.

(56) References Cited

U.S. PATENT DOCUMENTS

| | | | | |
|---|---|---|---|---|
| 3,156,820 | A * | 11/1964 | Reimer | 250/307 |
| 4,746,571 | A * | 5/1988 | Kelly | 428/328 |
| 5,486,701 | A * | 1/1996 | Norton et al. | 250/372 |
| 5,732,163 | A * | 3/1998 | Brandstetter et al. | 382/296 |
| 5,825,670 | A * | 10/1998 | Chernoff et al. | 702/85 |
| 6,066,849 | A | 5/2000 | Masnaghetti et al. | |
| 6,079,256 | A | 6/2000 | Bareket | |
| 6,384,408 | B1 | 5/2002 | Yee et al. | |
| 6,483,580 | B1 | 11/2002 | Xu et al. | |
| 6,515,287 | B2 | 2/2003 | Notte, IV | |
| 6,515,744 | B2 | 2/2003 | Wei | |
| 6,552,341 | B1 * | 4/2003 | Desplats et al. | 250/311 |
| 6,560,011 | B2 | 5/2003 | Chuang | |
| 6,570,154 | B1 | 5/2003 | Masnaghetti et al. | |
| 6,577,384 | B2 | 6/2003 | Wei et al. | |
| 6,578,961 | B2 | 6/2003 | Vaez-Iravani | |
| 6,586,733 | B1 | 7/2003 | Veneklasen et al. | |
| 6,587,282 | B1 | 7/2003 | Wang et al. | |
| 6,590,656 | B2 | 7/2003 | Xu et al. | |
| 6,602,727 | B1 * | 8/2003 | Rangarajan et al. | 438/14 |
| 6,603,541 | B2 | 8/2003 | Lange | |
| 6,608,294 | B2 * | 8/2003 | Nikitin et al. | 250/201.3 |
| 6,610,980 | B2 | 8/2003 | Veneklasen et al. | |
| 6,611,330 | B2 | 8/2003 | Lee et al. | |
| 6,623,991 | B2 | 9/2003 | Johnson et al. | |
| 6,642,726 | B2 * | 11/2003 | Weiner et al. | 324/751 |
| 6,650,415 | B2 | 11/2003 | Aspnes et al. | |
| 6,650,424 | B2 * | 11/2003 | Brill et al. | 356/601 |

(Continued)

*Primary Examiner*—Tarifur Chowdhury
*Assistant Examiner*—Jonathan D Cook
(74) *Attorney, Agent, or Firm*—Baker & McKenzie LLP

(57) ABSTRACT

Methods and systems for measurements of a substrate are provided. One system includes a non-optical subsystem configured to perform first measurements on a substrate. The system also includes an optical subsystem coupled to the non-optical subsystem. The optical subsystem is configured to perform second measurements on the substrate. In addition, the system includes a processor coupled to the subsystems. The processor is configured to calibrate one of the subsystems using the measurements performed by the other subsystem. One method includes performing first measurements on a substrate using a non-optical subsystem and performing second measurements on the substrate using an optical subsystem that is coupled to the non-optical subsystem. The method also includes calibrating one of the subsystems using the measurements performed by the other subsystem.

19 Claims, 5 Drawing Sheets

U.S. PATENT DOCUMENTS

| | | |
|---|---|---|
| 6,654,131 B2 | 11/2003 | Opsal et al. |
| 6,657,715 B2 | 12/2003 | Vaez-Iravani et al. |
| 6,664,546 B1 | 12/2003 | McCord et al. |
| 6,670,612 B1 | 12/2003 | Lorusso et al. |
| 6,677,586 B1 | 1/2004 | Nasser-Ghodsi et al. |
| 6,678,046 B2 | 1/2004 | Opsal |
| 6,687,008 B1 | 2/2004 | Peale et al. |
| 6,694,284 B1 * | 2/2004 | Nikoonahad et al. ........ 702/155 |
| 6,940,592 B2 * | 9/2005 | Borden et al. .............. 356/326 |
| 6,986,280 B2 * | 1/2006 | Muckenhirm ................ 73/104 |
| 2003/0224262 A1 * | 12/2003 | Lof et al. ..................... 430/22 |
| 2005/0030530 A1 * | 2/2005 | Nikitin et al. ........... 356/243.1 |
| 2005/0236569 A1 * | 10/2005 | Yamaguchi et al. ......... 250/311 |
| 2006/0076488 A1 * | 4/2006 | Ina ............................. 250/309 |

\* cited by examiner

METHODS AND SYSTEMS FOR OPTICAL AND NON-OPTICAL MEASUREMENTS OF A SUBSTRATE

PRIORITY CLAIM

This application claims priority to U.S. Provisional Application No. 60/546,907 entitled "Methods and Systems for Optical and Non-Optical Measurements of a Substrate," filed Feb. 23, 2004, which is incorporated by reference as if fully set forth herein.

BACKGROUND OF THE INVENTION

1. Field of the Invention

The present invention generally relates to methods and systems for optical and non-optical measurements of a substrate. Certain embodiments relate to methods and systems for performing measurements with a non-optical subsystem and an optical subsystem and for calibrating one of the subsystems using measurements performed by the other subsystem.

2. Description of the Related Art

The following descriptions and examples are not admitted to be prior art by virtue of their inclusion within this section.

Fabricating semiconductor devices such as logic and memory devices typically includes processing a substrate such as a semiconductor wafer using a number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

Throughout the fabrication process, characteristics of features formed on a wafer are measured for process monitoring and control purposes. For example, three-dimensional metrology of the profile of features on a wafer is often performed at various times during the process. In particular, the three-dimensional profile of photoresist features are often measured after a lithography step to determine if the features have characteristics that are within the specifications set for them (within spec). If the characteristics of the features are within spec, then the lithography step may be performed on additional wafers. On the other hand, if the characteristics of the features are not within spec, then one or more parameters of the lithography step may be altered. Another wafer may then be exposed in the lithography process, and the measurements described above may be performed. These steps may be repeated until the characteristics of the features are within spec.

As the dimensions of advanced semiconductor devices continue to shrink, the presence of defective features in the semiconductor devices increasingly limits the successful fabrication, or yield, of the semiconductor devices. For example, features formed on a wafer during the lithography step that are too large or too small may cause an open circuit or a short circuit in, or complete failure of, one or more semiconductor devices formed in subsequent processing. Because fabrication of a semiconductor device includes many complex process steps, the adverse effects of defective features on total yield may increase exponentially if a defective feature formed on a wafer in one process step causes additional defective features in subsequent process steps.

Accordingly, metrology of semiconductor wafers is and will continue to be of significant importance in semiconductor development and manufacturing. Furthermore, the ability of metrology tools or systems to measure a range of feature types precisely and accurately will determine how well characteristics of the features can be measured and, therefore, how well semiconductor fabrication processes can be monitored and controlled and how high the yield of a semiconductor fabrication process can be. Consequently, significant efforts have been and will continue to be made to increase the precision and accuracy of metrology systems by improving parameters of the systems such as resolution. There have also been significant efforts in improving the processing of metrology data to increase the accuracy with which features can be measured.

One common way to increase the accuracy of a feature measurement is to use a non-optical metrology technique for measurement of the feature instead of an optical metrology technique. One example of a non-optical metrology system that is commonly used to measure characteristics of features on wafers and reticles is a scanning electron microscope (SEM). Although electron beam metrology systems generally have greater resolution than optical metrology systems, there are several disadvantages to using such electron beam systems to measure characteristics of features on a reticle or a wafer. For example, existing SEM's used for critical dimension measurements use the apparent width of a structure to determine its dimensions. However, the apparent width of a feature is affected by many factors other than the actual physical width of the feature. For example, the interaction volume of the electrons in a given material and the related "edge-effect" can cause the apparent width of the feature to be much wider than its true physical dimensions. Similarly, the size of the measurement spot, the point spread function (PSF) of the system, the extraction field being used, and the geometry of the collector all affect the measured feature dimensions. Furthermore, the parameters of the SEM (as with other optical and non-optical measurement systems) may change over time thereby causing the measured sample properties to drift resulting in poor precision.

Accordingly, it would be advantageous to develop methods and systems for measurements of a feature on a substrate such as a wafer and a reticle that are more accurate and more precise than the optical and non-optical metrology systems that are currently available.

SUMMARY OF THE INVENTION

The following description of various embodiments of systems configured for measurement of a substrate, methods for measuring a substrate, and computer-implemented methods for calibrating a system is not to be construed in any way as limiting the subject matter of the appended claims.

An embodiment of the invention relates to a system configured for measurement of a substrate. The system includes a non-optical subsystem configured to perform first measurements on the substrate. The system also includes an optical subsystem coupled to the non-optical subsystem. The optical subsystem is configured to perform second measurements on the substrate. In addition, the system includes a processor coupled to the non-optical subsystem and the optical subsystem. The processor is configured to calibrate one of the subsystems using the measurements performed by the other subsystem.

In one embodiment, the optical subsystem may be configured as a scatterometer, a reflectometer, an ellipsometer, a polarized reflectometer, an interferometer, a spectroscopic reflectometer, a spectroscopic ellipsometer, a spectroscopic scatterometer, or some combination thereof. The non-optical subsystem may be configured as a scanning electron microscope.

In one embodiment, the optical subsystem may be further coupled to a substrate handler of the non-optical subsystem. In a different embodiment, the optical subsystem may be further coupled to a vacuum chamber of the non-optical subsystem. In a further embodiment, the optical subsystem may be further coupled to the non-optical subsystem by a transmission medium.

In some embodiments, the processor may also be configured to calibrate a different measurement system using the first measurements, the second measurements, or a combination thereof. In another embodiment, the processor may be configured to monitor one or more parameters of the non-optical subsystem using the first and second measurements. In an additional embodiment, the processor may be configured to monitor one or more parameters of the optical subsystem using the first and second measurements. In yet another embodiment, the processor may be configured to alter one or more parameters of the non-optical subsystem using the first and second measurements. In addition, or alternatively, the processor may be configured to alter one or more parameters of the optical subsystem using the first and second measurements.

In one embodiment, the first and second measurements are performed on a feature of the substrate that is optimized for the first and second measurements. In one such embodiment, the feature may be a target having repeating structures. In a different embodiment, the first measurements are performed on a first feature of the substrate that is optimized for the first measurements, and the second measurements are performed on a second feature of the substrate that is optimized for the second measurements. In such an embodiment, the second feature may include a target having grating structures.

In some embodiments, the processor may be configured to determine which of the subsystems is optimal for measuring a characteristic of a feature on the substrate and to route the substrate to the subsystem determined to be optimal. In another embodiment, the processor may be configured to use one of the measurements to determine if the other measurements will be performed. In a further embodiment, the processor may be configured to use one of the measurements to determine a site on the substrate at which the other measurements are to be performed. Each of the embodiments of the system described above may be further configured as described herein.

Another embodiment relates to a method for measuring a substrate. The method includes performing first measurements on the substrate using a non-optical subsystem. The method also includes performing second measurements on the substrate using an optical subsystem. The optical subsystem is coupled to the non-optical subsystem. In addition, the method includes calibrating one of the subsystems using the measurements performed by the other subsystem. The method described above may include any other step(s) described herein.

An additional embodiment relates to a computer-implemented method for calibrating a system. The method includes calibrating a first subsystem of the system using measurements performed on a substrate by a second subsystem of the system. One of the subsystems includes a non-optical subsystem, and the other subsystem includes an optical subsystem. The computer-implemented method described above may include any other step(s) described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
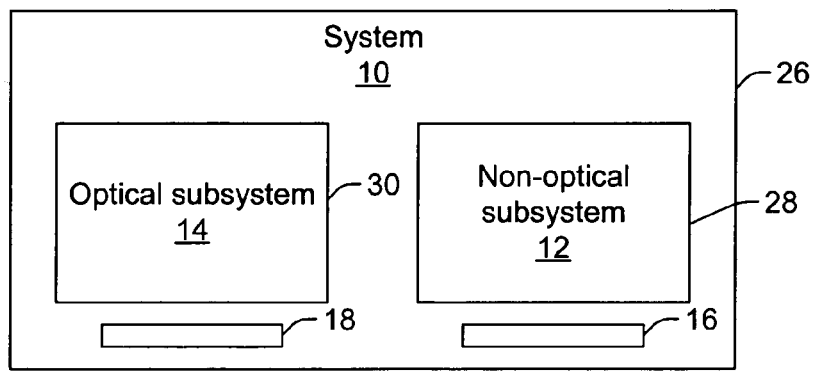
FIGS. 1-7 are schematic diagrams illustrating different embodiments of a system configured for measurement of a substrate.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "substrate" is generally defined as a wafer or a reticle. As used herein, the term "wafer" generally refers to a substrate formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include only the substrate. Such a wafer is commonly referred to as a "virgin wafer." Alternatively, a wafer may include one or more layers formed upon a substrate. For example, such layers may include, but are not limited to, a resist, a dielectric material, and a conductive material. A resist may include any material that may be patterned by an optical lithography technique, an e-beam lithography technique, or an X-ray lithography technique. Examples of a dielectric material include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., and CORAL™ commercially available from Novellus Systems, Inc., San Jose, Calif., "ultra-low k" dielectric materials such as "xerogels," and "high-k" dielectric materials such as tantalum pentoxide. In addition, examples of a conductive material include, but are not limited to, aluminum, polysilicon, and copper.

One or more layers formed on a wafer may be patterned or unpatterned. For example, a wafer may include a plurality of dies having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed. The term "semiconductor device" is used interchangeably herein with the term "integrated circuit." In addition, other devices such as microelectromechanical system (MEMS) devices and the like may also be formed on a wafer.

A "reticle" or a "mask" is generally defined as a substantially transparent substrate having substantially opaque regions formed thereon and configured in a pattern. The substrate may include, for example, a glass material such as quartz. The substantially opaque regions may be formed of a material such as chromium. A reticle may be disposed above a resist-covered wafer during an exposure step of a lithography process such that the pattern on the reticle may be transferred to the resist. For example, substantially opaque regions of the reticle may protect underlying regions of the resist from exposure to an energy source. Many different types of reticles are known in the art, and the term reticle as used herein is intended to encompass all types of reticles.

As used herein, the term "non-optical subsystem" generally refers to any non-optical measurement system that can be used to measure a characteristic of at least one of the substrates described herein. The non-optical measurement system may include any such system known in the art. For example, the non-optical subsystem may be configured as an electron-based measurement system such as a scanning electron microscope (SEM). Some SEM systems that are designed specifically to measure a critical dimension (CD) of features on a substrate are generally referred to as "CD-SEM systems," and such systems may be particularly useful in the systems and methods described herein. However, the SEM may have any one of the many different configurations known in the art. Examples of SEM configurations that may be included in the systems described herein and/or used in the methods described herein are illustrated in U.S. Pat. Nos. 6,066,849 to Masnaghetti et al., 6,384,408 to Yee et al., 6,515,287 to Notte IV, 6,570,154 to Masnaghetti et al., 6,586,733 to Veneklasen et al., 6,610,980 to Veneklasen et al., 6,664,546 to McCord et al., 6,677,586 to Nasser-Ghodsi et al., and 6,670,612 to Lorusso et al., which are incorporated by reference as if fully set forth herein. The non-optical subsystems described herein may be further configured as described in these patents. As will be obvious to one of ordinary skill in the art, the particular configuration of the SEM may vary depending on, for example, the substrate and features on the substrate that are to be measured using the SEM. In addition, the non-optical subsystem may include other non-optical based measurement systems such as other types of electron beam-based measurement systems, x-ray-based measurement systems, and ion beam-based measurement systems.

The term "optical subsystem" as used herein generally refers to any optical system that can be used to measure a characteristic of at least one of the substrates described herein. The optical subsystem may include any such system known in the art. For example, the optical subsystem may be configured as a scatterometer, a reflectometer, an ellipsometer, a polarized reflectometer, an interferometer, a spectroscopic reflectometer, a spectroscopic ellipsometer, a spectroscopic scatterometer, or some combination thereof. The optical subsystem may have any configuration known in the art. Examples of optical systems and configurations are illustrated in U.S. Pat. Nos. 6,079,256 to Bareket, 6,483,580 to Xu et al., 6,515,744 to Wei, 6,577,384 to Wei et al., 6,578,961 to Vaez-Iravani, 6,587,282 to Wang et al., 6,590, 656 to Xu et al., 6,603,541 to Lange, 6,611,330 to Lee et al., 6,623,991 to Johnson et al., 6,560,011 to Chuang et al., 6,650,415 to Aspnes et al., 6,654,131 to Opsal et al., 6,657,715 to Vaez-Iravani et al., 6,678,046 to Opsal, 6,687, 008 to Peale et al., and 6,694,284 to Nikoonahad et al., which are incorporated by reference as if fully set forth herein. The optical subsystems described herein may be configured as described in these patents.

Many other configurations for the optical systems described above are known in the art, and as will be obvious to one of ordinary skill in the art, the particular configuration used for the optical subsystem in the embodiments of the systems and methods described herein may vary depending on, for example, the substrates that are to be measured, the characteristics of the substrates that are to be measured, and the non-optical subsystem that is included in the system. For example, in one embodiment, the non-optical subsystem is configured as a SEM, and the feature to be measured includes a target having repeatable structures. In such an embodiment, a scatterometer may be used to perform measurements of such a feature. In addition, the optical subsystem may be configured as a non-imaging system and/or an imaging system. The optical subsystem may be further configured as a single wavelength system, a multi-wavelength system, and/or a spectroscopic system.

The term "feature" as used herein generally refers to a portion of a substrate selected for measurement (i.e., a "target" or a "measurement target"). One example of a feature that may be measured using the systems and methods described herein includes a target having repeating structures such as lines and spaces. For example, such a feature may be measured by an optical subsystem (e.g., a scatterometer) as well as a non-optical subsystem (e.g., a SEM). In addition, one or more characteristics of such a feature such as dimensions may be optimized for measurements by the optical subsystem and the non-optical subsystem. In this manner, this feature may be measured by both the optical and non-optical subsystems, and the results of such measurements may be used for calibration purposes as described further herein.

In other examples, the feature may include a feature that is optimized for measurement by only one of the subsystems (either a non-optical subsystem or an optical subsystem). One example of a feature that is optimized for measurements by an optical subsystem such as a scatterometer is a target having grating structures. However, a feature may include any other feature known in the art that can be formed on a wafer or a reticle and that can be measured by an optical subsystem and/or a non-optical subsystem.

The terms "first" and "second" are used herein only to distinguish between different measurements, different subsystems, etc. and are not to be construed in any other manner.

Turning now to the drawings, it is noted that FIGS. 1-7 and 9 are not drawn to scale. In particular, the scale of some of the elements of the figures are greatly exaggerated to emphasize characteristics of the elements. It is also noted that FIGS. 1-7 and 9 are not drawn to the same scale. Elements shown in more than one figure that may be similarly configured may have been indicated using the same reference numerals.

FIGS. 1-7 illustrate various embodiments of a system configured for measurement of a substrate. As shown in FIG. 1, in one embodiment, system 10 includes non-optical subsystem 12. The system also includes optical subsystem 14 coupled to non-optical subsystem 12. For example, optical subsystem 14 may be coupled to a substrate handler (not shown) of non-optical subsystem 12. In this manner, the subsystems may be coupled by a common substrate handler. In such an embodiment, the substrate handler may be configured to place a substrate onto and remove a substrate from stage 16 of non-optical subsystem 12. The substrate handler may include any mechanical or robotic assembly known in the art. In addition, the same substrate handler may be configured to place a substrate onto and remove a substrate from stage 18 of optical subsystem 14. In this manner, the optical subsystem and the non-optical subsystem share one substrate handler. Stages 16 and 18 may include any appropriate stages known in the art. In addition, stages 16 and 18 may be different types of stages or the same type of stage.

Figure 2:
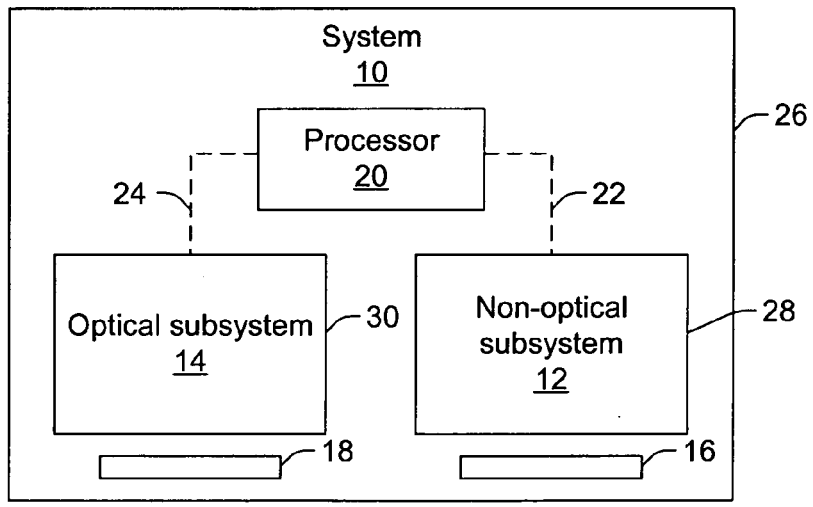

In an additional embodiment, the optical subsystem may be coupled to the non-optical subsystem by a common processor. For example, as shown in FIG. 2, system 10 includes processor 20 coupled to non-optical subsystem 12 and optical subsystem 14. In one particular example, processor 20 may be coupled to non-optical subsystem 12 by transmission medium 22 and to optical subsystem 14 by transmission medium 24. Transmission media 22 and 24 may include any transmission media known in the art and may include "wired" and "wireless" portions. The processor is preferably coupled to the non-optical subsystem and the optical subsystem such that the processor can receive output from the non-optical and optical subsystems. The output may include measurements performed by the non-optical and optical subsystems. The processor may also be configured to perform one or more functions using the measurements as described further herein. In addition, the processor is preferably coupled to the non-optical and/or the optical subsystems such that the processor can send data or instructions to the subsystems. For example, the processor may be configured to alter and/or control one or more parameters of one or both of the subsystems as described further herein.

As shown in FIG. 2, processor 20 is disposed within housing 26 of system 10. However, it is to be understood that processor 20 may alternatively be disposed outside of housing 26. The processor may be directly coupled to one or more components (not shown) of the subsystems (e.g., detectors, light sources, etc.) via transmission media 22 and 24. However, it is to be understood that the processor may be indirectly coupled to one or more of the components of the subsystems. For example, one or more electronic components (not shown) may be interposed between the processor and the subsystems. In one such example, a detector of the optical subsystem may be coupled to a component such as an analog-to-digital converter. The analog-to-digital converter may also be coupled to the processor such that after the analog-to-digital converter converts data generated by the detector, the data is passed on to the processor in digital form for further processing. The analog-to-digital converter may also operate in the reverse direction to send digital information from the processor in analog form to one or more components of the subsystem.

As shown in FIGS. 1 and 2, optical subsystem 14 and non-optical subsystem 12 are configured as individual measurement modules. The individual measurement modules may both be located in housing 26 of system 10. However, each of the individual measurement modules includes its own measurement head. The measurement head for each of the subsystems may or may not be disposed within its own housing or chamber. For example, non-optical subsystem 12 may be at least partially disposed within chamber 28. In some embodiments, chamber 28 may be a vacuum chamber. Such a chamber may be particularly suitable for an electron-beam based system such as a SEM. In addition, optical subsystem 14 may or may not be disposed within housing 30. Housing 30 may or may not be a vacuum chamber. For example, if the light used by the optical subsystem has a wavelength low enough so that it is substantially absorbed by air (e.g., wavelengths less than about 200 nm), housing 30 may be evacuated or purged such that the performance of the optical subsystem is not diminished by absorption of the light. Examples of systems that may be used for optical subsystem purging and/or evacuation are illustrated in U.S. patent application Ser. No. 10/845,958 by Fielden et al., filed on May 14, 2004, which is incorporated by reference as if fully set forth herein. The optical subsystems described herein may be further configured as described in this patent application. Otherwise, for wavelengths greater than about 200 nm, optical subsystem 14 may be disposed in an ambient environment (e.g., an environment with clean-room like conditions) within housing 30 or within housing 26. In this manner, housing 30 may or may not be included in the systems described herein.

Figure 3:
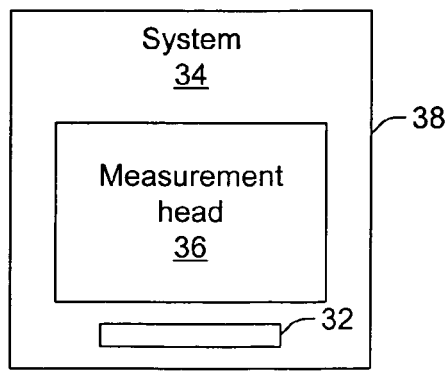

In another embodiment, as shown in FIG. 3, the optical subsystem may be coupled to the non-optical subsystem by common stage 32. In this manner, instead of each subsystem having its own individual stage, system 34 includes one stage 32 upon which a substrate may be disposed by a handler (not shown). While on the stage, the substrate may be measured by the optical subsystem and/or the non-optical subsystem. For example, the non-optical subsystem and the optical subsystem may be disposed within measurement head 36. Measurement head 36 and stage 32 may be disposed within outer housing 38 of system 34. Outer housing 38 may be configured as described above with respect to housing 26. Therefore, the measurement head may be configured to perform measurements on a substrate using the non-optical subsystem and the optical subsystem. The measurements performed by the non-optical subsystem and the optical subsystem may be performed substantially simultaneously or sequentially. In addition, the measurements performed by the non-optical subsystem and the optical subsystem may be performed in approximately the same location on the substrate substantially simultaneously or sequentially.

Alternatively, the optical subsystem and the non-optical subsystem may be disposed in individual, separate measurement heads, as described above, both of which are coupled to one stage. Therefore, in such an embodiment, the optical and non-optical subsystems will be spaced apart laterally with respect to the substrate. In such an embodiment, different locations on the substrate can be measured simultaneously by the optical and non-optical subsystems. In addition, the same measurement location on the substrate may be measured sequentially by the optical and non-optical subsystems. After measurements by one or both subsystems, the substrate may be removed from the stage. In this manner, the optical and non-optical subsystems may share one stage. Stage 32 may include any appropriate stage known in the art.

Figure 4:
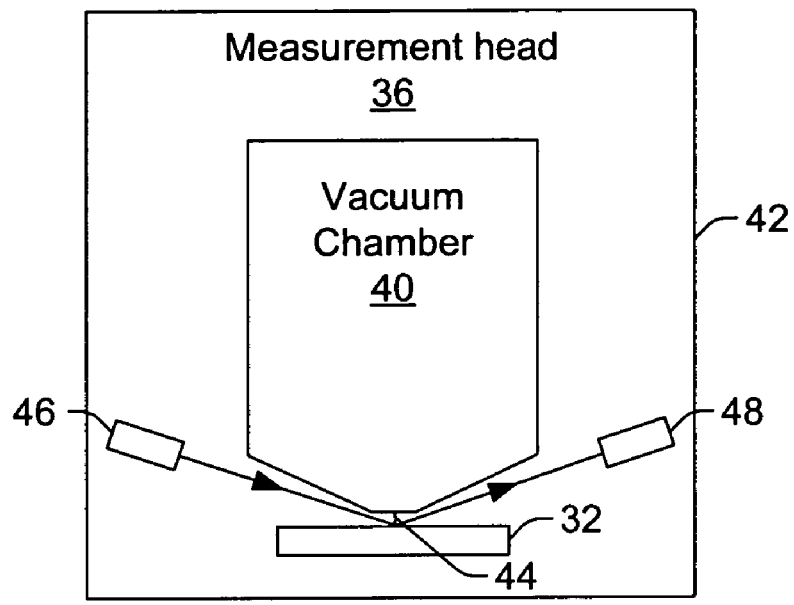

Since at least one of the subsystems in measurement head 36 is a non-optical subsystem, in some embodiments, the measurement head may include a vacuum chamber. One embodiment of such a measurement head is illustrated in FIG. 4. As shown in FIG. 4, measurement head 36 includes vacuum chamber 40. Vacuum chamber 40 may house one or more components of the non-optical subsystem such as an electron column (not shown). In fact, in one such embodiment, vacuum chamber 40 may be configured as the electron column. In such an embodiment, measurement chamber 36 may include outer housing 42. A vacuum (e.g., a vacuum that is lower than the vacuum in vacuum chamber 40) may also be maintained within outer housing 42. In this manner, stage 32 may be disposed within at least low vacuum conditions thereby reducing the interference that electrons 44 are exposed to as they travel between the electron column and a substrate (not shown) on stage 32. In addition, the distance between the aperture from which the electrons exit the electron column and the substrate is preferably kept at a minimum.

The optical subsystem is also disposed within outer housing 42. For example, as shown in FIG. 4, the optical subsystem may include at least light source 46 and detector 48. Typically, the optical subsystem will include additional optical components such as a collector, which are not shown in FIG. 4 for the sake of simplicity. Light source 46 may include any appropriate light source known in the art. In general, the light source (possibly in combination with other components of an illumination subsystem) is configured to direct light to a substrate disposed on stage 32. Detector 48 may include any appropriate detector known in the art. Detector 48 (possibly in combination with other optical components) is generally configured to detect light returned from the substrate disposed on stage 32. In addition, although one particular configuration of the optical subsystem is shown in FIG. 4, it is to be understood that the optical subsystem may be configured as described further above.

As shown in FIG. 4, both light source 46 and detector 48 are disposed within outer housing 42. In addition, as shown in FIG. 4, the optical and non-optical subsystems are directed to the same measurement location on a substrate. In this manner, the optical and non-optical subsystems may perform measurements on the substrate at the same measurement location substantially simultaneously or sequentially. In a different embodiment, both subsystems may be disposed within housing 42, but may be directed to different measurement locations on the substrate. For example, the subsystems may be laterally spaced apart from one another within housing 42. In this manner, the optical and non-optical subsystems may perform measurements at different locations on the substrate substantially simultaneously and/or measurements at the same location on the substrate sequentially.

In a different embodiment, one or more components of the optical subsystem may be coupled to vacuum chamber 40 (and possibly even disposed within vacuum chamber 40). In this manner, the light of the optical subsystem may be transmitted to and/or from a substrate through the vacuum chamber. In such an embodiment, the light may enter the vacuum chamber via an optical window fitted into an outer wall of the vacuum chamber. The light may be directed by one or more optical components disposed within the vacuum chamber. In addition, the light may pass through an aperture of the vacuum chamber as the electrons do such that the light may be incident on the substrate. In such embodiments, the light may or may not be coaxial with the electron beam. Examples of systems in which a light beam and an electron beam can be directed to the surface of a specimen coaxially are illustrated in U.S. Patent Application Ser. No. 60/555,170 by Nasser-Ghodsi et al., filed on Mar. 22, 2004, which is incorporated by reference as if fully set forth herein. Furthermore, in some such embodiments, the optical subsystem and the non-optical subsystem may be configured such that the electrons and the light may be incident on the substrate at substantially the same time or at different times. Therefore, as with other embodiments described herein, the optical subsystem and the non-optical subsystem may be configured to perform measurements substantially simultaneously or sequentially. System 34 and measurement head 36 may be further configured as described herein. For example, system 34 includes a processor (not shown in FIG. 3 or 4) that is configured as described further herein.

Figure 5:
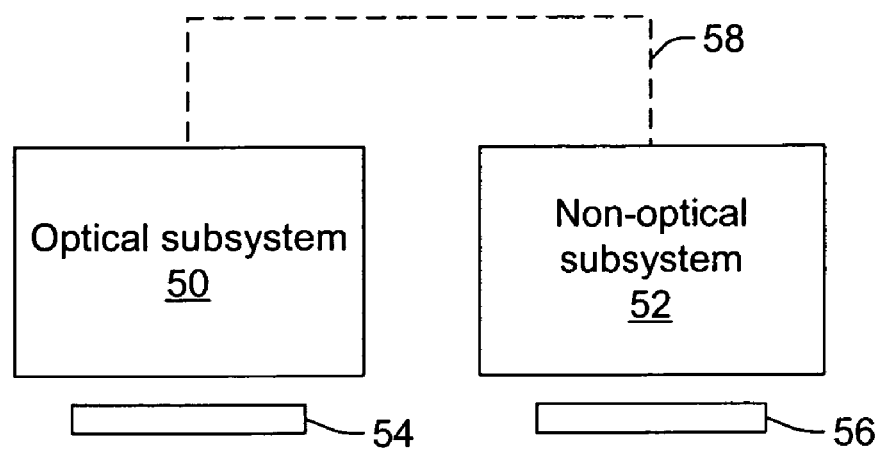

In another embodiment, a system configured for measurement may include an optical subsystem and a non-optical subsystem coupled to each other by a transmission medium. The transmission medium serves as an information link between the two subsystems. For example, as shown in FIG. 5, a system includes optical subsystem 50 and non-optical subsystem 52. In this embodiment, as shown in FIG. 5, optical subsystem 50 may be coupled to stage 54, and non-optical subsystem 52 may be coupled to stage 56. Stages 54 and 56 may include any suitable mechanical or robotic assemblies known in the art. Optical subsystem 50 and non-optical subsystem 52 may also have their own processors, wafer handlers, housings, power sources, etc. (not shown). As such, each subsystem may be configured as a measurement system physically separate from the other subsystem. In addition, optical subsystem 50 may be located remotely from non-optical subsystem 52.

However, regardless of their locations, the optical subsystem and the non-optical subsystem may be coupled by transmission medium 58. Transmission medium 58 may include any appropriate transmission medium known in the art and may include "wired" and "wireless" portions. In one particular embodiment, a processor (not shown) of optical subsystem 50 may be coupled by transmission medium 58 to a processor (not shown) of non-optical subsystem 52. In this manner, measurements and other information may be sent between processors of the subsystems across the transmission medium. The system shown in FIG. 5 may be further configured as described herein. In addition, the processors of subsystems 50 and 52 may be configured as described further herein.

Figure 6:
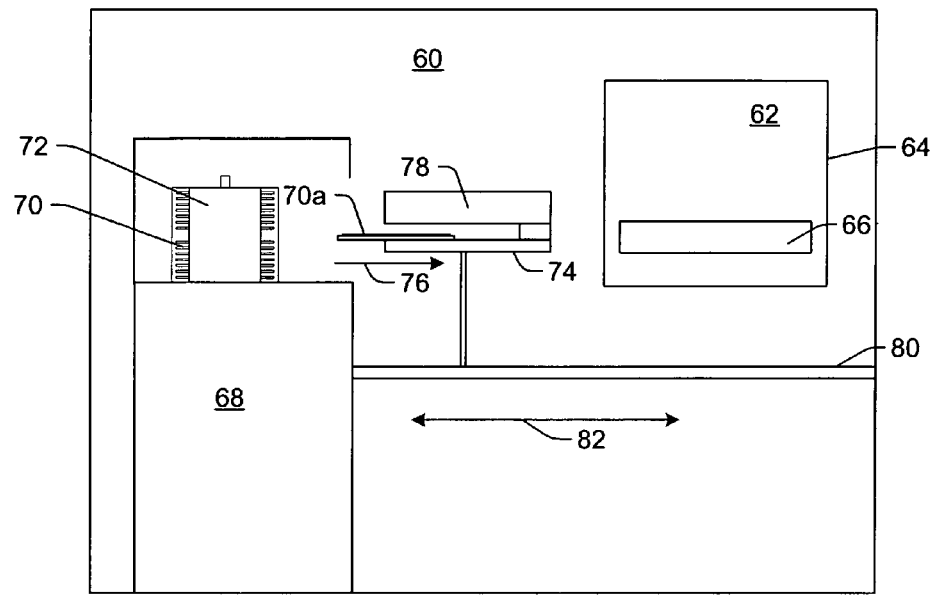

In a different embodiment, the optical subsystem may be coupled to the non-optical subsystem by being mounted on a substrate handler of the non-optical subsystem. One example of such an embodiment is illustrated in FIG. 6. As shown in FIG. 6, system 60 includes non-optical subsystem 62. Non-optical subsystem 62 may be configured as described herein. Non-optical subsystem 62 may include housing 64, which in some embodiments may be a vacuum chamber. For example, if the non-optical subsystem is an electron beam-based subsystem, then the housing may be configured as a vacuum chamber. Alternatively, a vacuum chamber (not shown) of the non-optical subsystem may be disposed within housing 64. Housing 64 may also include door 66. Door 66 may be configured to open when a substrate is being placed into the housing or is being removed from the housing. In addition, door 66 may be configured to close after a substrate has been placed into the housing or has been removed from the housing.

In some embodiments, the non-optical subsystem may include a load lock (not shown) into which a substrate is moved after entering the housing. Once a substrate has been placed into the load lock, the load lock will be evacuated to create a vacuum in the load lock. The vacuum in the load lock is generally lower than the vacuum in the measurement area of the subsystem. However, having substrates enter the measurement area through such a load lock may reduce the amount of time that it takes to create the predetermined vacuum conditions in the measurement area of the subsystem. In addition, the substrate may remain in the load lock until the conditions in the load lock are substantially the same as the conditions in the measurement area.

In one such embodiment, instead of mounting the optical subsystem to the substrate handler as described further herein, the optical subsystem may be coupled to the load lock. For example, the optical subsystem may be mounted on the load lock such that it is positioned above a substrate in the load lock. Since the substrate will be in the load lock until it can be sufficiently evacuated, measurements on the substrate can be performed by the optical subsystem during this time. In one embodiment, the optical subsystem may be disposed within the load lock. However, the optical subsystem is preferably mounted outside of the load lock. In such an embodiment, a portion of the load lock located between the optical subsystem and the substrate may be fitted with an optical window such that the optical subsystem may perform measurements on the substrate while it is located in the load lock.

In another embodiment, one optical subsystem may be coupled to the load lock, and another optical subsystem may be coupled to the substrate handler as described further herein. The optical subsystems may have the same or different configurations. In addition, the optical subsystems may be configured to perform the same and/or different measurements on the substrates.

Substrates that are to be measured by the optical and/or non-optical system may be placed into load module 68 either manually or automatically. In the example shown in FIG. 6, substrates 70 are wafers disposed in wafer cassette 72. The system includes substrate handler 74. The substrate handler may include any mechanical or robotic assembly known in the art. The substrate handler is configured to remove a substrate from wafer cassette 72. For example, substrate 70*a* may be moved from wafer cassette 72 and into the substrate handler 74 in direction 76 such that substrate 70*a* is wholly located within and supported by the substrate handler. Optical subsystem 78 is mounted on substrate handler 74 such that it is spaced above substrate 70*a*.

As substrate 70*a* is being moved into the substrate handler, measurements on the substrate may be performed by optical subsystem 74. The measurements may also or alternatively be performed after the substrate has been completely moved into the substrate handler and as the substrate handler moves along track 80 in direction 82. The substrate handler may move along track 80 in direction 82 to move the substrate to non-optical inspection subsystem 62. Substrate handler 74 may also move in a direction opposite to direction 82 in the plane of the paper, for instance, to remove substrates 70 from different positions within wafer cassette 72. System 60 may be further configured as described herein. For example, system 60 also includes a processor (not shown in FIG. 6) that may be configured as described herein.

Furthermore, each of the systems described herein may include more than one optical subsystem (not shown) and/or more than one non-optical subsystem (not shown). For example, a system configured for measurement of a substrate may include two non-optical subsystems. The non-optical subsystems may have the same or different configurations. The non-optical subsystems may be used to perform the same or different measurements in parallel. Alternatively, the non-optical subsystems may be used to perform different measurements in series. Such a system may also include one or more optical subsystems. For example, one optical subsystem may be coupled to the two non-optical subsystems. The optical subsystem may be configured to perform measurements on substrates before and/or after the substrates are measured by one or both of the non-optical subsystems. Such an embodiment may be advantageous in instances such as when the optical subsystem has a higher throughput than the non-optical subsystems.

In another embodiment, a system configured for measurement of a substrate may include two or more optical subsystems. The two or more optical subsystems may be configured to perform different measurements on a substrate. Such an embodiment may be advantageous in instances such as when substrates having vastly different features or characteristics are to be measured. One of the optical subsystems may be optimized for measurements of some of the features or characteristics, and another of the subsystems may be optimized for measurements of other types of features or characteristics. Two or more optical subsystems may be arranged within one measurement head or may be arranged within different measurement heads. In addition, the two or more optical subsystems may be coupled to the same stage or different stages. The two or more optical subsystems may share other or additional components described herein.

Each of the non-optical subsystems shown in FIGS. 1-6 and described above is configured to perform first measurements on a substrate. In addition, each of the optical subsystems shown in FIGS. 1-6 and described above is configured to perform second measurements on the substrate. The first measurements are performed on at least one feature on the substrate. The second measurements may also be performed on at least one of the features that is measured by the non-optical subsystem. In this manner, the optical subsystem and the non-optical subsystem both perform measurements on at least one common feature.

The feature that is measured by both subsystems is preferably optimized for both measurement subsystems. For example, if the non-optical subsystem is configured as a SEM, and the optical subsystem is configured as a scatterometer, then the feature that is measured by both subsystems may include a target having repeating structures. The repeating structures may have any shape known in the art such as lines and spaces. The feature that is measured by both subsystems may be formed on a calibration wafer that is reusable and that has been previously measured using a traceable measurement technique. Alternatively, the feature that is measured by both subsystems may be formed on a product wafer. In such an embodiment, the feature may be a test feature that has been optimized for measurement by both subsystems or a device feature. In addition, the measurements of features that are performed by both subsystems may be performed on each substrate that is measured, a subset of the substrates that are measured, a calibration substrate, or some combination thereof. One or more characteristics of the feature may be determined using the measurements of the optical subsystem and/or the non-optical subsystem. Such characteristics include, but are not limited to, a critical dimension such as a width or any other measurable characteristic of the feature such as a height, a sidewall angle or a three-dimensional profile, a period, etc.

The measurements of the common feature may then be used to calibrate one of the subsystems. For example, measurements of a feature performed by the optical subsystem may be used to calibrate the non-optical subsystem. Alternatively, measurements of a feature performed by the non-optical subsystem may be used to calibrate the optical subsystem. The calibration itself may be performed in any manner known in the art such as determining a correction factor using the measurements of the two subsystems. In this manner, the systems described herein provide accurate, meaningful calibration for one or both of the subsystems. As such, the systems and methods described herein provide accurate measurements of the true physical dimensions and characteristics of substrates.

The processors described herein are, therefore, configured to calibrate one of the subsystems using the measurements performed by the other subsystem. For example, the processor may be configured to calibrate the non-optical subsystem using the measurements performed by the optical subsystem. The processor may also be configured to calibrate the optical subsystem using measurements performed by the non-optical subsystem. The processor may be further configured to calibrate the optical and non-optical subsystems using the first and second measurements, respectively.

After the subsystems have been calibrated, both subsystems may be used to perform additional measurements on different features on the substrate. The different features that are measured by one of the subsystems may or may not be features that are measured by the other subsystem. For example, each calibrated subsystem may be used to measure features on the substrate for which it is optimized. In the example of a SEM coupled to a scatterometer, the scatterometer may be used to perform measurements of one or more targets on the substrate that have grating structures. The SEM may also be used to perform measurements of these one or more targets. Alternatively, or in addition, the SEM may be used to perform measurements of other targets on the substrate that do not have grating structures.

In some embodiments, the measurements performed by one or both of the subsystems may be used to calibrate a different measurement system. Such a calibration may also be performed by any of the processors described herein. In particular, a processor described herein may be configured to calibrate a different measurement system using the first measurements, the second measurements, or a combination thereof. The different measurement system may be a non-optical and/or optical subsystem. The calibration itself may be performed in any manner known in the art as described above.

Figure 7:
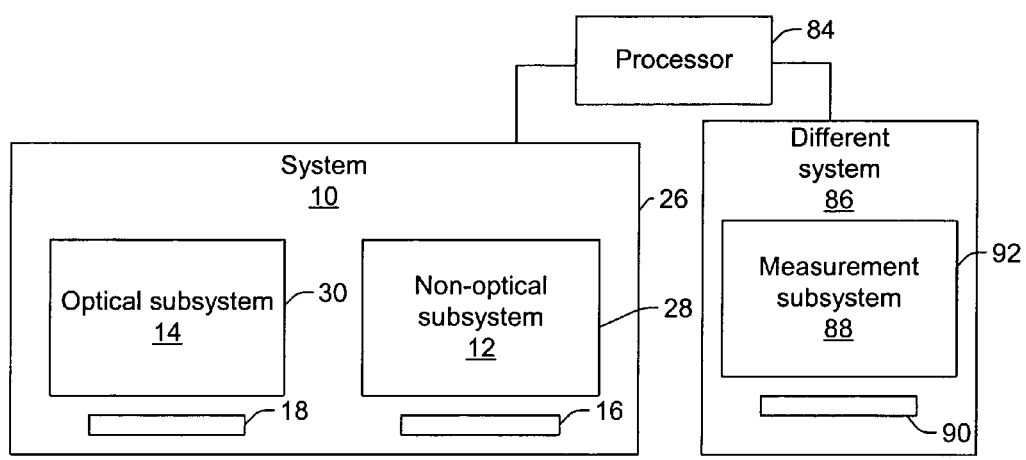

One embodiment of a system that may perform such a calibration is illustrated in FIG. 7. This system includes measurement system 10, which is configured as shown in FIG. 1. However, the measurement system included in this embodiment may have any other configuration described herein. Processor 84 is coupled to system 10 as shown in FIG. 7. Processor 84 may be coupled to the system as described above. For example, the processor may be coupled to optical subsystem 14 and non-optical subsystem 12 by transmission media 24 and 22, respectively, as shown in FIG. 1. Alternatively, processor 84 may be coupled to a processor of system 10 (such as processor 20 as shown in FIG. 2) by a transmission medium.

In this manner, processor 84 may be coupled to one or more processors of one or more measurement systems and may be configured to cross-calibrate one or more of the measurement systems using measurements performed by other measurement systems. For example, as shown in FIG. 7, processor 84 is also coupled to different measurement system 86. In one embodiment, processor 84 may be coupled to a processor (not shown) of measurement system 86 by a transmission medium. Alternatively, processor 84 may be coupled directly to measurement subsystem 88 of measurement system 86 by a transmission medium (not shown). In either embodiment, processor 84 is configured to calibrate measurement subsystem 88 of system 86 using measurements performed by optical subsystem 14 and/or non-optical subsystem 12.

Measurement subsystem 88 may be configured as an optical subsystem and/or a non-optical subsystem and may be further configured as described above. For example, measurement subsystem 88 may include stage 90 and housing 92, each of which may be configured as described above. If measurement subsystem 88 is a non-optical subsystem, processor 84 may use measurements by optical subsystem 14 to calibrate measurement subsystem 88. On the other hand, if measurement subsystem 88 is an optical subsystem, processor 84 may use measurements by non-optical subsystem 12 to calibrate measurement subsystem 88. Processor 84 may also be configured to perform other functions such as routing information between measurement systems, managing a fab database that includes measurements performed by multiple measurement systems, etc. Other processors described herein may be configured to perform similar functions.

In a particularly advantageous embodiment, a processor may be used to calibrate multiple subsystems of two or more measurement systems using one set of measurement data. For example, if non-optical subsystem 12 and measurement subsystem 88 are configured as SEMs, measurements performed by optical subsystem 14 may be used to calibrate both SEMs. In this manner, different measurement subsystems of different measurement systems may be calibrated using the same measurements performed on the same feature. Cross-calibration of multiple measurement systems may be particularly advantageous for semiconductor development and manufacturing applications in which multiple measurement systems are used to measure the same substrate at different points in the fabrication process or the same types of features on different substrates. For instance, such cross-calibration would reduce the uncertainty in measurements that are performed on the same type of wafers using different measurement systems. In addition, such cross-calibration of multiple measurement systems would increase the flexibility of the semiconductor development and manufacturing processes. For example, different lots of wafers for the same product do not have to be measured on the same measurement system to ensure uniformity in the measurements.

Any of the processors described herein may be configured to perform calibrations as described above in addition to other functions. For example, a processor as described herein may be configured to monitor one or more parameters of a non-optical subsystem using measurements performed by the non-optical subsystem and/or the optical subsystem. In another example, a processor may be configured to monitor one or more parameters of an optical subsystem using measurements performed by the optical subsystem and/or the non-optical subsystem. In a further embodiment, a processor may be configured to monitor one or more parameters of a non-optical subsystem as well as one or more parameters of an optical subsystem as described above. In this manner, the systems described herein may not only calibrate the measurement subsystems, but may also monitor parameter(s) of the measurement subsystem over time for "drift" in the parameter(s).

The systems described herein may also be configured to correct for drift in the parameter(s) of the optical subsystem and/or the non-optical subsystem. In this manner, the systems and methods described herein provide improved precision for substrate measurements even in the presence of changes in the parameters of the measurement tool. For example, any of the processors described herein may be configured to alter one or more parameters of the non-optical subsystem using measurements performed by the non-optical subsystem and/or the optical subsystem. In a different example, a processor as described herein may be configured to alter one or more parameters of an optical subsystem using measurements performed by the optical subsystem and/or the non-optical subsystem. Furthermore, each of the processors described herein may be configured to alter parameter(s) of the non-optical subsystem and the optical subsystem as described above.

In another embodiment, any of the processors described herein may be configured to determine which of the subsystems is optimal for measuring a characteristic of a feature on the substrate. For example, the processor may use information about the feature, which may have been generated by the system, to determine if one of the measurement subsystems is better suited for measuring one or more characteristics of the feature. The information about the feature may include expected characteristics of the feature such as, but not limited to, expected shape, expected critical dimension, and expected period. For example, if the feature is expected to have a critical dimension that is substantially below the resolution of the optical subsystem, then the non-optical subsystem may be selected for measurement of the feature since the non-optical subsystem will generally have better resolution capabilities than the optical subsystem. Therefore, an appropriate measurement subsystem may be selected based on approximate or expected characteristics of a feature thereby providing increased measurement flexibility and optimization.

Such an embodiment of the processor may also be configured to route the substrate to the subsystem that is determined to be optimal for the measurements. In the above example, since the non-optical subsystem is slated for measurement of the substrate, the processor may route the substrate to the non-optical subsystem by controlling a substrate handler and possibly other components of the measurement system. The substrate handler may be controlled using any method or system known in the art.

In some embodiments, any of the processors described herein may be configured to determine which measurements will be performed on a substrate. Such decisions may be based on measurements performed by the optical subsystem and/or the non-optical subsystem. In particular, the processor may be configured to use one of the measurements to determine if the other measurements will be performed. In another example, the processor may be configured to use one of the measurements to determine a site on the substrate at which the other measurements are to be performed. In one particular example, if the optical measurement results indicate that there may be a problem with the substrate or feature(s) on the substrate, then the processor may determine that the non-optical subsystem should measure the substrate to get further information about the potential problem. In a different example, the non-optical subsystem may perform measurements on a substrate. If the non-optical measurement results are significantly different than the expected characteristics of the substrate or feature(s) on the substrate, then the processor may determine that the optical subsystem should measure the substrate to double check the measurements in order to determine if the non-optical subsystem is functioning properly.

As will be obvious to one of ordinary skill in the art, there are many variables that may be taken into account by the processor when deciding if a substrate should be measured or re-measured using a different measurement subsystem. The processor may be configured to use a rules database to determine what measurements should be performed on a substrate based on measurement results. Such a rules database may be tailored by individual users to reflect decisions they would like the processor to make in various situations. The processor may then make these decisions based on measurement results automatically (i.e., without intervention from the user).

In a similar way, any of the processors described herein may be configured to determine further processing that should be performed on a substrate based on the measurement results. For example, a processor may determine that the substrate should be processed to correct defective features on the substrate, processed to remove one or more layers on the substrate such that a process may be repeated on the substrate but with different parameters, processed to resume manufacturing of devices on the substrate, processed to review the defective features on the substrate, etc. The embodiments of the systems described above may be further configured as described herein.

Figure 8:
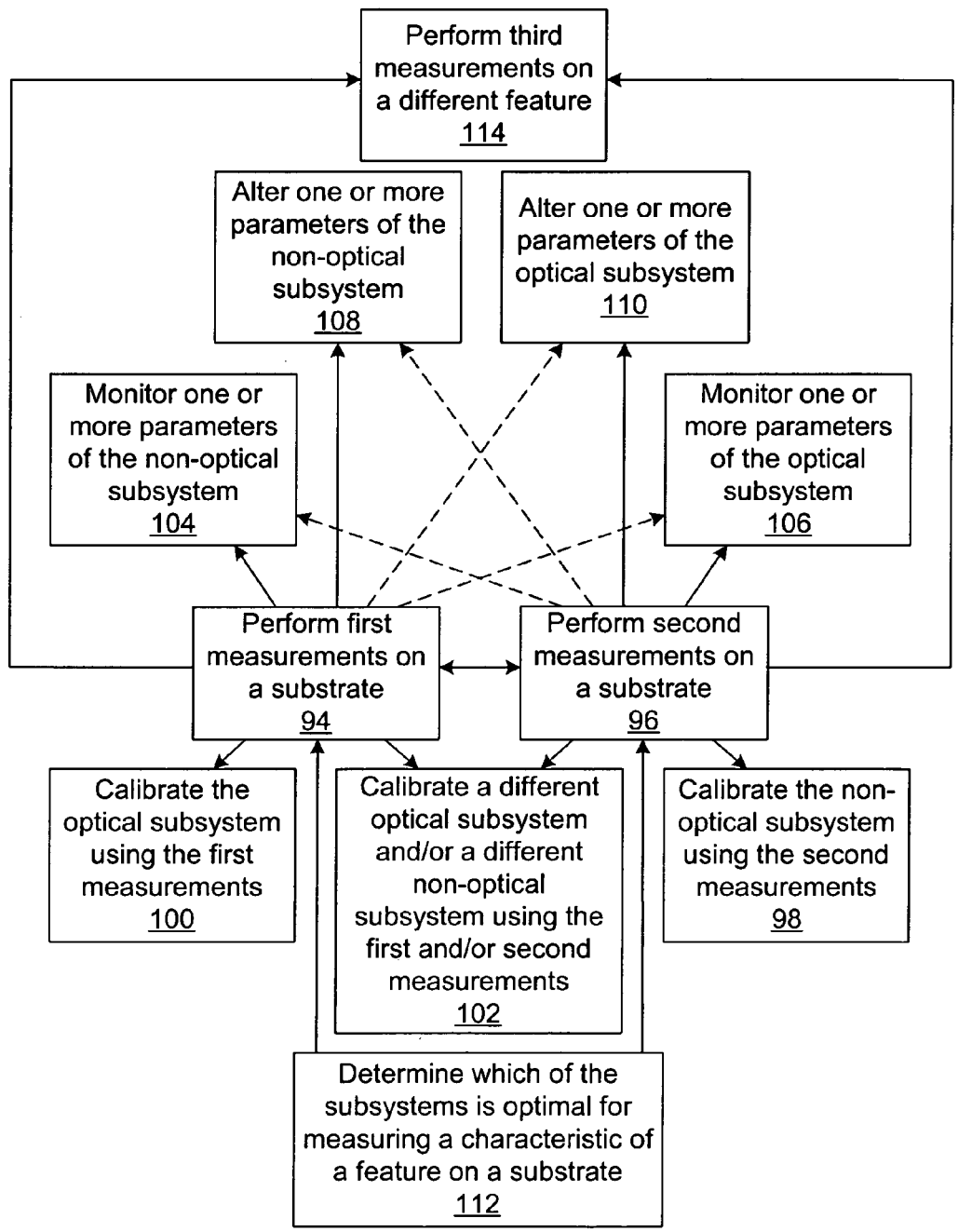
FIG. 8 is a flow chart illustrating one embodiment of a method for measuring a substrate.

FIG. 8 illustrates one embodiment of a method for measuring a substrate. It is to be noted that many of the steps shown in FIG. 8 are not essential to practice of the method. One or more steps may be added to or omitted from the method illustrated in FIG. 8, and the method can still be practiced within the scope of this embodiment.

The method includes performing first measurements on the substrate using a non-optical subsystem, as shown in step 94. The method also includes performing second measurements on the substrate using an optical subsystem, as shown in step 96. The optical subsystem is coupled to the non-optical subsystem. The optical subsystem may be coupled to the non-optical subsystem as described further above.

The first and second measurements may be performed on a feature that is optimized for the first and second measurements. For example, in the case of a SEM and a scatterometer, the feature may be a target having repeating structures. In another embodiment, the first measurements may be performed on one feature that is optimized for the first measurements, and the second measurements may be performed on another feature on the substrate that is optimized for the second measurements. In one such embodiment, if the optical subsystem is configured as a scatterometer, the feature that is measured by the optical subsystem may be a target having grating structures.

The method further includes calibrating one of the subsystems using the measurements performed by the other subsystem. In one such embodiment, the method may include calibrating the non-optical system using the second measurements performed by the optical subsystem, as shown in step 98. Calibrating the non-optical subsystem may be performed as described further above. In another embodiment, the method may include calibrating the optical subsystem using the first measurements performed by the non-optical subsystem, as shown in step 100. In addition, the method may include calibrating both the optical subsystem and the non-optical subsystem using the first and second measurements, respectively.

Some embodiments of the method may include calibrating a different optical subsystem and/or a different non-optical subsystem using the first and/or second measurements, as shown in step 102. The non-optical subsystem and the optical subsystem may be arranged in one system as described further above. The different optical subsystem and/or the different non-optical subsystem may be arranged in a different measurement system as further described above. Therefore, the method may include cross-calibration of different measurements systems, which is advantageous as further described above.

One embodiment of the method may include monitoring one or more parameters of the non-optical subsystem using the first and/or second measurements, as shown in step 104. Some embodiments of the method may include monitoring one or more parameters of the optical subsystem using the first and/or second measurements, as shown in step 106. In addition, the method may also include monitoring one or more parameters of the non-optical subsystem and the optical subsystem as described above. Monitoring the parameter(s) of the non-optical subsystem and/or the optical subsystem may be performed to detect drift in the parameter(s) of the subsystem(s).

Another embodiment of the method may include altering one or more parameters of the non-optical subsystem using the first and/or second measurements, as shown in step 108. An additional embodiment of the method may include altering one or more parameters of the optical subsystem using the first and/or second measurements, as shown in step 110. Furthermore, the method may include altering one or more parameters of the non-optical subsystem and the optical subsystem as described above. Altering the parameter(s) of the non-optical subsystem and/or the optical subsystem may be performed such that drift in the parameter(s) of the subsystem(s) is corrected. In this manner, the methods described herein provide substantially accurate measurement results from both optical and non-optical subsystems through calibration, monitoring, and correction.

The method may also include determining which of the subsystems is optimal for measuring a characteristic of a feature on the substrate, as shown in step 112. Such a determination may be performed as described further above. In such an embodiment, the method may also include routing the substrate to the subsystem that is determined to be optimal for the measurements. Routing the substrate to one of the subsystems may be performed as described above. Some of the embodiments of the method may also include using the first measurements to determine if the second measurements will be performed and/or using the second measurements to determine if the first measurements will be performed. In an additional embodiment, the method may include using the first measurements to determine which site(s) on the substrate are to be measured using the optical subsystem and/or using the second measurements to determine which site(s) on the substrate are to be measured using the non-optical subsystem. Such determinations may be performed as described further above.

The methods described herein may also include measuring additional features on the substrate using one or both of the subsystems. For example, the first and second measurements described above may be performed on one feature on the substrate. The method may also include performing third measurements on a different feature on the substrate, as shown in step 114. The third measurements on the different feature may be performed using the non-optical subsystem and/or the optical subsystem. For example, the subsystem that is optimized for measurement of the different feature may vary depending on the characteristics of the different feature. Therefore, the different feature may be measured using only the subsystem that is optimized for its measurement. Alternatively, both subsystems may be used to measure the different feature. The embodiment of the method shown in FIG. 8 may include any other step(s) described herein or known in the art.

Another embodiment relates to a computer-implemented method for calibrating a system. Many of the steps of the computer-implemented method are illustrated in FIG. 8, and therefore further illustration of the computer-implemented method is not provided herein. The computer-implemented method includes calibrating a first subsystem of the system using measurements performed on a substrate by a second subsystem of the system. One of the subsystems includes a non-optical subsystem, and the other subsystem includes an optical subsystem. The non-optical subsystem and the optical subsystem may be configured as described above. The non-optical subsystem and the optical subsystem may be coupled according to any of the embodiments described above. The computer-implemented method may include any other step(s) described herein.

Figure 9:
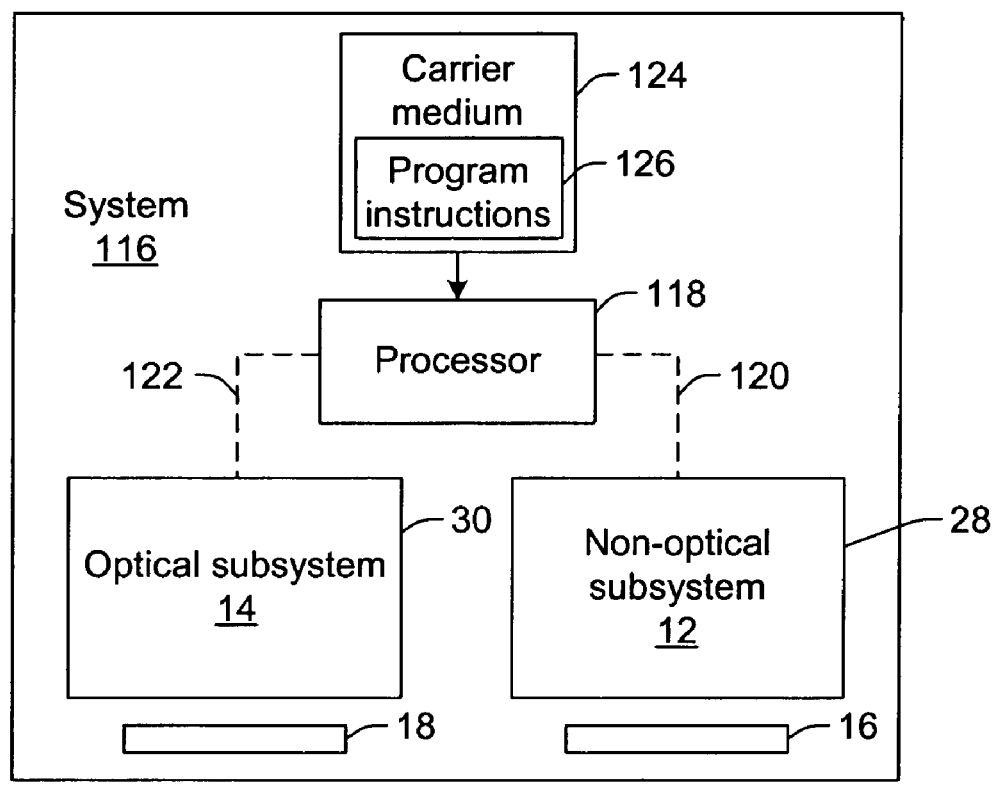
FIG. 9 is a schematic diagram illustrating one embodiment of a system that is configured to perform a computer-implemented method for calibrating a system.

FIG. 9 illustrates one embodiment of a system that may be used to perform any of the embodiments of the computer-implemented method described above. For example, system 116 includes non-optical subsystem 12 and optical subsystem 14. Non-optical subsystem 12 and optical subsystem 14 may be configured as described above. For example, non-optical subsystem 12 may be disposed within housing 28 and may be coupled to stage 16. Optical subsystem 14 may be disposed within housing 30 and may be coupled to stage 18. Although one embodiment of non-optical subsystem 12 and optical subsystem 14 is shown in FIG. 9, it is to be understood that system 116 may include any of the embodiments of a non-optical subsystem and an optical subsystem described herein.

System 116 also includes processor 118. Processor 118 is coupled to non-optical subsystem 12 and optical subsystem 14, for example, by transmission media 120 and 122, respectively. The transmission media may include any of the transmission media described above or known in the art. Processor 118 may be further coupled to non-optical subsystem 12 and optical subsystem 14 as further described herein. System 116 also includes carrier medium 124. Carrier medium 124 may be coupled to processor 118 using any method or device known in the art.

Program instructions 126 implementing methods such as those described herein may be transmitted over or stored on carrier medium 124. The carrier medium may be a transmission medium such as a wire, cable, or wireless transmission link, or a signal traveling along such a wire, cable, or link. The carrier medium may also be a storage medium such as a read-only memory, a random access memory, a magnetic or optical disk, or a magnetic tape.

In an embodiment, processor 118 may be configured to execute the program instructions to perform a computer-implemented method according to any of the above embodiments. The processor may take various forms, including an image computer, a parallel processor, a personal computer system, mainframe computer system, workstation, network appliance, Internet appliance, personal digital assistant ("PDA"), television system or other device. In general, the term "computer system" may be broadly defined to encompass any device having one or more processors, which executes instructions from a memory medium.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired. System 116 may be further configured as described herein.

Further modifications and alternative embodiments of various aspects of the invention may be apparent to those skilled in the art in view of this description. For example, methods and systems for optical and non-optical measurements of a substrate are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured for measurement of a substrate, comprising:
    a non-optical subsystem configured to perform first measurements on the substrate;
    an optical subsystem coupled to the non-optical subsystem, wherein the optical subsystem is configured to perform second measurements on the substrate; and
    a processor coupled to the non-optical subsystem and the optical subsystem, wherein the processor is configured to calibrate one of the subsystems using the measurements performed by the other subsystem, and wherein the processor is further configured to use one of the measurements to determine if the other measurements will be performed.

2. The system of claim 1, wherein the optical subsystem is further configured as a scatterometer, a reflectometer, an ellipsometer, a polarized reflectometer, an interferometer, a spectroscopic reflectometer, a spectroscopic ellipsometer, a spectroscopic scatterometer, or some combination thereof.

3. The system of claim 1, wherein the non-optical subsystem is further configured as a scanning electron microscope.

4. The system of claim 1, wherein the processor is further configured to calibrate a different measurement system using the first measurements, the second measurements, or a combination thereof.

5. The system of claim 1, wherein the processor is further configured to monitor one or more parameters of the non-optical subsystem using the first and second measurements.

6. The system of claim 1, wherein the processor is further configured to monitor one or more parameters of the optical subsystem using the first and second measurements.

7. The system of claim 1, wherein the processor is further configured to alter one or more parameters of the non-optical subsystem using the first and second measurements.

8. The system of claim 1, wherein the processor is further configured to alter one or more parameters of the optical subsystem using the first and second measurements.

9. The system of claim 1, wherein the first and second measurements are performed on a feature of the substrate that is optimized for the first and second measurements.

10. The system of claim 9, wherein the feature comprises a target having repeating structures.

11. The system of claim 1, wherein the first measurements are performed on a first feature of the substrate that is optimized for the first measurements, and wherein the second measurements are performed on a second feature of the substrate that is optimized for the second measurements.

12. The system of claim 11, wherein the second feature comprises a target having grating structures.

13. The system of claim 1, wherein the processor is further configured to determine which of the subsystems is optimal for measuring a characteristic of a feature on the substrate and to route the substrate to the subsystem determined to be optimal.

14. The system of claim 1, wherein the processor is further configured to use one of the measurements to determine a site on the substrate at which the other measurements are to be performed.

15. The system of claim 1, wherein the optical subsystem is further coupled to a substrate handler of the non-optical subsystem.

16. The system of claim 1, wherein the optical subsystem is further coupled to a vacuum chamber of the non-optical subsystem.

17. The system of claim 1, wherein the optical subsystem is further coupled to the non-optical subsystem by a transmission medium.

18. A method for measuring a substrate, comprising:
    performing first measurements on the substrate using a non-optical subsystem;
    performing second measurements on the substrate using an optical subsystem, wherein the optical subsystem is coupled to the non-optical subsystem;
    calibrating one of the subsystems using the measurements performed by the other subsystem; and
    using one of the measurements to determine if the other measurements will be performed.

19. A computer-implemented method for calibrating a system, comprising:
    calibrating a first subsystem of the system using measurements performed on a substrate by a second subsystem of the system, wherein one of the subsystems comprises a non-optical subsystem, and wherein the other subsystem comprises an optical subsystem; and
    using measurements of one of the subsystems to determine if measurements of the other subsystem will be performed.

* * * * *